United States Patent [19]

Wiegand et al.

[11] Patent Number: 5,629,155
[45] Date of Patent: May 13, 1997

[54] HIGH-AFFINITY OLIGONUCLEOTIDE LIGANDS TO IMMUNOGLOBULIN E (IGE)

[75] Inventors: Torsten W. Wiegand; Diane Tasset; Larry Gold, all of Boulder, Colo.

[73] Assignee: NeXstar Pharmaceuticals, Inc., Boulder, Colo.

[21] Appl. No.: 317,403

[22] Filed: Oct. 3, 1994

Related U.S. Application Data

[63] Continuation-in-part of Ser. No. 714,131, Jun. 10, 1991, Pat. No. 5,475,096, which is a continuation-in-part of Ser. No. 536,428, Jun. 11, 1990, abandoned, and a continuation-in-part of Ser. No. 964,624, Oct. 21, 1992, Pat. No. 5,496,938.

[51] Int. Cl.$^6$ .............................. C12Q 1/68; C12P 19/34
[52] U.S. Cl. .............................. 455/6; 435/91.2; 935/77; 935/78
[58] Field of Search .................. 435/6, 91.2; 935/77; 935/78

[56] References Cited

U.S. PATENT DOCUMENTS 5,270,163  12/1993  Gold et al. ................................. 435/6

FOREIGN PATENT DOCUMENTS

| 2183661A | 6/1987 | United Kingdom . |
|---|---|---|
| WO89/06694 | 7/1989 | WIPO . |
| WO91/19813 | 12/1991 | WIPO . |
| WO92/14843 | 9/1992 | WIPO . |

OTHER PUBLICATIONS

Nagpal et al., Autoimmunity 8(1): 59–64 (1990).
Dombrowicz et al. (1993) Cell 75:969–976.
Pieken et al. (1991) Science 253:314–317.
Sutton and Gould (1993) Nature 366:421–428.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. SCI. USA 63:805.
Levisohn and Spiegelman Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Chang et al. (1990) Bio/Technology 8:122.
Davis et al. (1991) Bio/Technology 9:53.
Haak–Frendscho et al. (1993) J. Immunology 151:351.
Haba and Nisonoff (1994) Proc. Natl. Acad. Sci. USA 91:604.
Peng et al. (1992) J. Immunology 148:129.
Presta et al. (1993) J. Immunology 151:2623.
Saban et al. (1994) J. Allergy Clin. Immunol. 94:836.
Stampfli et al. (1994) Eur. J. Immunology 24:2161.

*Primary Examiner*—Stephanie W. Zitomer
*Attorney, Agent, or Firm*—Swanson & Bratschun, L.L.C.

[57] ABSTRACT

This invention discloses high-affinity oligonucleotide ligands to human Immunoglobulin E (IgE), specifically RNA ligands having the ability to bind to IgE, and the methods for obtaining such ligands. The ligands are capable of inhibiting the interaction of IgE with its receptor.

5 Claims, No Drawings

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:1:

```
GGGAGGACGA  UGCGGNNNNN  NNNNNNNNNN  NNNNNNNNNN  NNNNNNNNNN          50
NNNNNCAGAC  GACUCGCCCG  A                                           71
```

( 2 ) INFORMATION FOR SEQ ID NO:2:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:2:

```
GGGAGGACGA  UGCGGNNNNN  NNNNNNNNNN  NNNNNNNNNN  NNNNNNNNNN          50
NNNNNNNNNN  NNNNNNNNNN  NNNNNCAGAC  GACUCGCCCG  A                   91
```

( 2 ) INFORMATION FOR SEQ ID NO:3:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
TAATACGACT  CACTATAGGG  AGGACGATGC  GG                              32
```

( 2 ) INFORMATION FOR SEQ ID NO:4:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
TCGGGCGAGT  CGTCTG                                                  16
```

( 2 ) INFORMATION FOR SEQ ID NO:5:

( i ) SEQUENCE CHARACTERISTICS:
        ( A ) LENGTH: 40

( B ) TYPE: nucleic acid
        ( C ) STRANDEDNESS: single
        ( D ) TOPOLOGY: linear ( x i ) SEQUENCE DESCRIPTION: SEQ ID NO:5:

CCGAAGCTTA ATACGACTCA CTATAGGGAG GACGATGCGG    40

( 2 ) INFORMATION FOR SEQ ID NO:6:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO:6:

GCCGGATCCT CGGGCGAGTC GTCTG    25

( 2 ) INFORMATION FOR SEQ ID NO:7:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:7:

GGGAGGACGA TGCGGGUGUG AAUGGUGUUG UGAGGUUACU GUACUUCGGU    50

GGCUGCAGAC GACTCGCCCG A    71

( 2 ) INFORMATION FOR SEQ ID NO:8:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:8:

GGGAGGACGA TGCGGGUGUG AACGGUGUUG UGAGGUUACU GUACUUCGGU    50

GGCUGCAGAC GACTCGCCCG A    71

( 2 ) INFORMATION FOR SEQ ID NO:9:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:9:

```
GGGAGGACGA  TGCGGGUGCG  AAUGGUGUUG  UGAGGAGCCU  AAAUACGCGA         50

UUGGUCAGAC  GACTCGCCCG  A                                          71
```

( 2 ) INFORMATION FOR SEQ ID NO:10:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:10:

```
GGGAGGACGA  TGCGGGUGUG  AAUGGUGUUG  UGAGGACUCG  GAAGUUCCCC         50

AGGGCCAGAC  GACTCGCCCG  A                                          71
```

( 2 ) INFORMATION FOR SEQ ID NO:11:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:11:

```
GGGAGGACGA  TGCGGGUGUG  AAUGGUGUUG  CGAGGCAUGC  AGGAGGCGCU         50

GUGGUCAGAC  GACTCGCCCG  A                                          71
```

( 2 ) INFORMATION FOR SEQ ID NO:12:

( i ) SEQUENCE CHARACTERISTICS:
    ( A ) LENGTH: 71
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:12:

```
GGGAGGACGA  TGCGGGUGUG  AAUGGUGUCG  UGAGGACUUA  UCAGGCUCCG         50

UGGUGCAGAC  GACTCGCCCG  A                                          71
```

( 2 ) INFORMATION FOR SEQ ID NO:13:

( i ) SEQUENCE CHARACTERISTICS:
    ( A ) LENGTH: 69
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:

( D ) OTHER INFORMATION: All U's are 2'-NH₂ uracil ( x i ) SEQUENCE DESCRIPTION: SEQ ID NO:13:

GGGAGGACGA TGCGGGUGUG AAUGGUGUUG UGAGGUUACU GCACUUCGGC    50

GCUCAGACGA CTCGCCCGA    69

( 2 ) INFORMATION FOR SEQ ID NO:14:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ cytosine ( i x ) FEATURE:
        ( D ) OTHER INFORMATION: All U's are 2'-NH₂ uracil ( x i ) SEQUENCE DESCRIPTION: SEQ ID NO:14:

GGGAGGACGA TGCGGGUGUG CAUGGUGUUG UGAGGCUGAG UAUAGGGCC    50

UGCGUCAGAC GACTCGCCCG A    71

( 2 ) INFORMATION FOR SEQ ID NO:15:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ cytosine ( i x ) FEATURE:
        ( D ) OTHER INFORMATION: All U's are 2'-NH₂ uracil ( x i ) SEQUENCE DESCRIPTION: SEQ ID NO:15:

GGGAGGACGA TGCGGGUGUG AAUGGUGUCG UGAGGAUGGA UUCGACAUGA    50

GCGAUCAGAC GACTCGCCCG A    71

( 2 ) INFORMATION FOR SEQ ID NO:16:

( i ) SEQUENCE CHARACTERISTICS:
        ( A ) LENGTH: 94
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ cytosine ( i x ) FEATURE:
        ( D ) OTHER INFORMATION: All U's are 2'-NH₂ uracil ( x i ) SEQUENCE DESCRIPTION: SEQ ID NO:16:

GGGAGGACGA TGCGGGUGUC AAUGGUGUUG CGAGGCAAAA AUAACCAGCG    50

CAUAUUCUCG GCCAUGUUGG CGUGCAUACA GACGACTCGC CCGA    94

( 2 ) INFORMATION FOR SEQ ID NO:17:

( i ) SEQUENCE CHARACTERISTICS:
        ( A ) LENGTH: 90
        ( B ) TYPE: nucleic acid
        ( C ) STRANDEDNESS: single
        ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:17:

```
GGGAGGACGA TGCGGGUGCG AAUGGUGUUG UGAGGAGUGA AUAUAGGUGG      50
AUACCCCUUA ACAACUGCGU GGGUCAGACG ACTCGCCCGA                 90
```

( 2 ) INFORMATION FOR SEQ ID NO:18:

( i ) SEQUENCE CHARACTERISTICS:
        ( A ) LENGTH: 90
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:18:

```
GGGAGGACGA TGCGGGUGUG AAUGGUGUUG UGAGGUUCUC GACUGUUUGU      50
GUCUAGCCGU ACUUUAGCCU CGGCCAGACG ACTCGCCCGA                 90
```

( 2 ) INFORMATION FOR SEQ ID NO:19:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:19:

```
GGGAGGACGA TGCGGGUGAG GGGCGAAUGG AGAACAUGAG ACAAGGAGAA      50
UGCGGCAGAC GACTCGCCCG A                                     71
```

( 2 ) INFORMATION FOR SEQ ID NO:20:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:20:

```
GGGAGGACGA TGCGGGUGUG GGGCGAAUGA GAAACGUUAC CAGGAAAUGC      50
GACUGCAGAC GACTCGCCCG A                                     71
```

( 2 ) INFORMATION FOR SEQ ID NO:21:

( i ) SEQUENCE CHARACTERISTICS:
        ( A ) LENGTH: 71

(B) TYPE: nucleic acid
(C) STRANDEDNESS: single
(D) TOPOLOGY: linear (ix) FEATURE:
(D) OTHER INFORMATION: All C's are 2'-NH$_2$ cytosine (ix) FEATURE:
(D) OTHER INFORMATION: All U's are 2'-NH$_2$ uracil (xi) SEQUENCE DESCRIPTION: SEQ ID NO:21:

GGGAGGACGA TGCGGGAGUG GGGCGAAGGU AAUGUUGAGA CGAUGUAAGA    50

CUGGUCAGAC GACTCGCCCG A    71

(2) INFORMATION FOR SEQ ID NO:22:

(i) SEQUENCE CHARACTERISTICS:
(A) LENGTH: 71
(B) TYPE: nucleic acid
(C) STRANDEDNESS: single
(D) TOPOLOGY: linear (ix) FEATURE:
(D) OTHER INFORMATION: All C's are 2'-NH$_2$ cytosine (ix) FEATURE:
(D) OTHER INFORMATION: All U's are 2'-NH$_2$ uracil (xi) SEQUENCE DESCRIPTION: SEQ ID NO:22:

GGGAGGACGA TGCGGGCGUG GGGCGAUUCA UAUCAACUGC UUAAGGUCAC    50

GGGUCCAGAC GACTCGCCCG A    71

(2) INFORMATION FOR SEQ ID NO:23:

(i) SEQUENCE CHARACTERISTICS:
(A) LENGTH: 91
(B) TYPE: nucleic acid
(C) STRANDEDNESS: single
(D) TOPOLOGY: linear (ix) FEATURE:
(D) OTHER INFORMATION: All C's are 2'-NH$_2$ cytosine (ix) FEATURE:
(D) OTHER INFORMATION: All U's are 2'-NH$_2$ uracil (xi) SEQUENCE DESCRIPTION: SEQ ID NO:23:

GGGAGGACGA TGCGGGUGCG GGGCGAGUAU AUGAAACUUG GCUUGGUAAU    50

GAUCAGAAGU AGUGAGAACU GGGUGCAGAC GACTCGCCCG A    91

(2) INFORMATION FOR SEQ ID NO:24:

(i) SEQUENCE CHARACTERISTICS:
(A) LENGTH: 90
(B) TYPE: nucleic acid
(C) STRANDEDNESS: single
(D) TOPOLOGY: linear (ix) FEATURE:
(D) OTHER INFORMATION: All C's are 2'-NH$_2$ cytosine (ix) FEATURE:
(D) OTHER INFORMATION: All U's are 2'-NH$_2$ uracil (xi) SEQUENCE DESCRIPTION: SEQ ID NO:24:

GGGAGGACGA TGCGGGAGUG GGGCGUAGGA UUUGCCACUU GGAUUUGGAC    50

AGUGAGCAUC AGAGUCAUCA CCGCCAGACG ACTCGCCCGA    90

( 2 ) INFORMATION FOR SEQ ID NO:25:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:25:

```
GGGAGGACGA  TGCGGGAGUG  GGGCGGAAUA  ACUAUGUGUG  CGUAAUUGUC     50
CUGUCGCGGU  GUCACGAACC  UUGUGCAGAC  GACTCGCCCG  A               91
```

( 2 ) INFORMATION FOR SEQ ID NO:26:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:26:

```
GGGAGGACGA  TGCGGGUGUG  GGGCGGAUAA  UGAGUGAACA  GAGUGAAAUU     50
CCAGCGUACG  CAGACUGUGC  UGUCGCAGAC  GACTCGCCCG  A               91
```

( 2 ) INFORMATION FOR SEQ ID NO:27:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:27:

```
GGGAGGACGA  TGCGGGAGUG  GGGCGAUGAG  AGAGAUCAGA  GAACUAGAAG     50
UGAUACAAAA  UCUGAGGUUG  UUGCGCAGAC  GACTCGCCCG  A               91
```

( 2 ) INFORMATION FOR SEQ ID NO:28:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:28:

```
GGGAGGACGA  TGCGGGUGUG  GGGCGGAUAA  UGAGUGAACA  GAGUGAAAUU     50
```

CCAGUGUAGC CAGACUGUGC UGUCGCAGAC GACTCGCCCG A              91

( 2 ) INFORMATION FOR SEQ ID NO:29:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:29:

GGGAGGACGA TGCGGUCCAU CGAUUAGGCG GUCGUGCUGG UGUAGUGUGU     50

AGUGGCAGAC GACTCGCCCG A                                    71

( 2 ) INFORMATION FOR SEQ ID NO:30:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:30:

GGGAGGACGA TGCGGACGGU AGUCUGGUAG GCGCUGUGAC GGCGAGAAUC     50

CGGACCAGAC GACTCGCCCG A                                    71

( 2 ) INFORMATION FOR SEQ ID NO:31:

( i ) SEQUENCE CHARACTERISTICS:
        ( A ) LENGTH: 70
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:31:

GGGAGGACGA TGCGGGUAUC GGUACGUGUU GGCUUGGGAA GGGGUCCGAC     50

GGUGCAGACG ACTCGCCCGA                                      70

( 2 ) INFORMATION FOR SEQ ID NO:32:

( i ) SEQUENCE CHARACTERISTICS:
        ( A ) LENGTH: 71
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:32:

GGGAGGACGA TGCGGACGGU AGUCUGGUAG GCGCUGUGAC GCCGAGAAUC    50

CGGAUCAGAC GACTCGCCCG A    71

( 2 ) INFORMATION FOR SEQ ID NO:33:

( i ) SEQUENCE CHARACTERISTICS:
        ( A ) LENGTH: 69
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:33:

GGGAGGACGA TGCGGAGACG CGUGAACACU AGUAUCACAG UUAAGGAUGC    50

GCGCAGACGA CTCGCCCGA    69

( 2 ) INFORMATION FOR SEQ ID NO:34:

( i ) SEQUENCE CHARACTERISTICS:
        ( A ) LENGTH: 70
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:34:

GGGAGGACGA TGCGGACCGC CCGUCGAGGG CUAGGCGUAG AGUCUAACCG    50

GUGCCAGACG ACTCGCCCGA    70

( 2 ) INFORMATION FOR SEQ ID NO:35:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ cytosine ( i x ) FEATURE:
        ( D ) OTHER INFORMATION: All U's are 2'-NH$_2$ uracil ( x i ) SEQUENCE DESCRIPTION: SEQ ID NO:35:

GGGAGGACGA TGCGGGCGGG GAACAGACGG CUCAGAGCGG CACGAUUGUC    50

AGCCAGCAAU UAUAUCGUGU UGAUGCAGAC GACTCGCCCG A    91

( 2 ) INFORMATION FOR SEQ ID NO:36:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:

( D ) OTHER INFORMATION: All C's are 2'-NH₂ cytosine ( i x ) FEATURE:
    ( D ) OTHER INFORMATION: All U's are 2'-NH₂ uracil ( x i ) SEQUENCE DESCRIPTION: SEQ ID NO:36:

```
GGGAGGACGA TGCGGGCCAC GCGUGGUUAG GGAUCGCGGA CAGCACAAAU        50
CGAAUUUGAU UCGCACCUGG ACGGUCAGAC GACTCGCCCG A                 91
```

( 2 ) INFORMATION FOR SEQ ID NO:37:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ cytosine ( i x ) FEATURE:
        ( D ) OTHER INFORMATION: All U's are 2'-NH₂ uracil ( x i ) SEQUENCE DESCRIPTION: SEQ ID NO:37:

```
GGGAGGACGA TGCGGAACAG CACGAGUGUA CCUAAGACAG GCGAUGGCAC        50
UCGUGGUCGA AAUCAUAUAG UGAUGCAGAC GACTCGCCCG A                 91
```

( 2 ) INFORMATION FOR SEQ ID NO:38:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ cytosine ( i x ) FEATURE:
        ( D ) OTHER INFORMATION: All U's are 2'-NH₂ uracil ( x i ) SEQUENCE DESCRIPTION: SEQ ID NO:38:

```
GGGAGGACGA TGCGGGACGG GGGCGGAAUC AUGCAUGUGA GCGAACAGAG        50
AGAGAGCCGU GUAUCCAUUC GUGGUCAGAC GACTCGCCCG A                 91
```

( 2 ) INFORMATION FOR SEQ ID NO:39:

( i ) SEQUENCE CHARACTERISTICS:
        ( A ) LENGTH: 91
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ cytosine ( i x ) FEATURE:
        ( D ) OTHER INFORMATION: All U's are 2'-NH₂ uracil ( x i ) SEQUENCE DESCRIPTION: SEQ ID NO:39:

```
GGGAGGACGA TGCGGAGGCG ACGAGGUGGA CAGGGGUAGG GAAGAUCGUC        50
UGAAGUAUGC GUCCUUCCAG CCCGUCAGAC GACTCGCCCG A                 91
```

( 2 ) INFORMATION FOR SEQ ID NO:40:

( i ) SEQUENCE CHARACTERISTICS:
        ( A ) LENGTH: 91
        ( B ) TYPE: nucleic acid ( C ) STRANDEDNESS: single
( D ) TOPOLOGY: linear ( i x ) FEATURE:
( D ) OTHER INFORMATION: All C's are 2'-NH$_2$ cytosine ( i x ) FEATURE:
( D ) OTHER INFORMATION: All U's are 2'-NH$_2$ uracil ( x i ) SEQUENCE DESCRIPTION: SEQ ID NO:40:

| | | | | |
|---|---|---|---|---|
| GGGAGGACGA | TGCGGUGGAG | CCUUUAGGGG | GAAUAGUUGG | CAGAAUUGCA | 50 |
| GCUCAUGUAA | UCUCGACUGU | GUGUGCAGAC | GACTCGCCCG | A | 91 |

( 2 ) INFORMATION FOR SEQ ID NO:41:

( i ) SEQUENCE CHARACTERISTICS:
( A ) LENGTH: 90
( B ) TYPE: nucleic acid
( C ) STRANDEDNESS: single
( D ) TOPOLOGY: linear ( i x ) FEATURE:
( D ) OTHER INFORMATION: All C's are 2'-NH$_2$ cytosine ( i x ) FEATURE:
( D ) OTHER INFORMATION: All U's are 2'-NH$_2$ uracil ( x i ) SEQUENCE DESCRIPTION: SEQ ID NO:41:

| | | | | |
|---|---|---|---|---|
| GGGAGGACGA | TGCGGUGGAG | CCUUUAGGGG | GAUCGCACCU | GAUCAAAGAC | 50 |
| GCAGUAUCGA | UAGACUUGCG | UGCCCAGACG | ACTCGCCGA | | 90 |

( 2 ) INFORMATION FOR SEQ ID NO:42:

( i ) SEQUENCE CHARACTERISTICS:
( A ) LENGTH: 13
( B ) TYPE: nucleic acid
( C ) STRANDEDNESS: single
( D ) TOPOLOGY: linear ( i x ) FEATURE:
( D ) OTHER INFORMATION: All C's are 2'-NH$_2$ cytosine ( i x ) FEATURE:
( D ) OTHER INFORMATION: All U's are 2'-NH$_2$ uracil ( x i ) SEQUENCE DESCRIPTION: SEQ ID NO:42:

GGGNGNGGNG GGG                                                        13

( 2 ) INFORMATION FOR SEQ ID NO:43:

( i ) SEQUENCE CHARACTERISTICS:
( A ) LENGTH: 20
( B ) TYPE: nucleic acid
( C ) STRANDEDNESS: single
( D ) TOPOLOGY: linear ( i x ) FEATURE:
( D ) OTHER INFORMATION: All C's are 2'-NH$_2$ cytosine ( i x ) FEATURE:
( D ) OTHER INFORMATION: All U's are 2'-NH$_2$ uracil ( i x ) FEATURE:
( D ) OTHER INFORMATION: N at position 4 is 3-5
nucleotides ( i x ) FEATURE:
( D ) OTHER INFORMATION: N at position 6 is U or C ( i x ) FEATURE:
( D ) OTHER INFORMATION: N at position 9 is A or U ( x i ) SEQUENCE DESCRIPTION: SEQ ID NO:43:

GUGUGAAUGG UGUUGUGAGG								20

( 2 ) INFORMATION FOR SEQ ID NO:44:

( i ) SEQUENCE CHARACTERISTICS:
    ( A ) LENGTH: 10
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:44:

GUGUGGGGCG								10

( 2 ) INFORMATION FOR SEQ ID NO:45:

( i ) SEQUENCE CHARACTERISTICS:
    ( A ) LENGTH: 32
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:45:

AGGACGAUGC GGGUGUGAAU GGUGUUGUGA GG						32

( 2 ) INFORMATION FOR SEQ ID NO:46:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:46:

AGGACGAUGC GGGUGUGGGG CG							22

( 2 ) INFORMATION FOR SEQ ID NO:47:

( i ) SEQUENCE CHARACTERISTICS:
    ( A ) LENGTH: 35
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ cytosine ( i x ) FEATURE:
    ( D ) OTHER INFORMATION: All U's are 2'-NH$_2$ uracil ( x i ) SEQUENCE DESCRIPTION: SEQ ID NO:47:

GGGAGGACGA UGCGGGUGUG AAUGGUGUUG UGAGG						35

(2) INFORMATION FOR SEQ ID NO:48:

(i) SEQUENCE CHARACTERISTICS:
      (A) LENGTH: 25
      (B) TYPE: nucleic acid
      (C) STRANDEDNESS: single
      (D) TOPOLOGY: linear (ix) FEATURE:
      (D) OTHER INFORMATION: All C's are 2'-NH$_2$ cytosine (ix) FEATURE:
      (D) OTHER INFORMATION: All U's are 2'-NH$_2$ uracil (xi) SEQUENCE DESCRIPTION: SEQ ID NO:48:

GGGAGGACGA UGCGGGUGUG GGGCG  25

HIGH-AFFINITY OLIGONUCLEOTIDE LIGANDS TO IMMUNOGLOBULIN E (IGE)

RELATED APPLICATIONS

This application is a Continuation-in-Part of U.S. patent application Ser. No. 07/714,131, filed Jun. 10, 1991, entitled Nucleic Acid Ligands, now U.S. Pat. No. 5,475,096, which is a Continuation-in Part of U.S. patent application Ser. No. 07/536,428, filed Jun. 11, 1990, entitled Systematic Evolution of Ligands by Exponential Enrichment, now abandoned, and U.S. patent application Ser. No. 07/964,624, filed Oct. 21, 1992, entitled Methods of Producing Nucleic Acid Ligands now U.S. Pat. No. 5,496,938.

FIELD OF THE INVENTION

Described herein are methods for identifying and preparing high-affinity nucleic acid ligands to Immunoglobulin E (IgE). The method utilized herein for identifying such nucleic acid ligands is called SELEX, an acronym for Systematic Evolution of Ligands by EXponential enrichment. Specifically disclosed herein are high-affinity nucleic acid ligands. The invention includes high-affinity RNA ligands which bind to IgE and inhibit its ability to interact with the IgE FcεRI receptor.

BACKGROUND OF THE INVENTION

Stimulation of mast cells and basophils upon contact of allergy-specific IgE antibodies with antigens, called immediate hypersensitivity, is one of the most powerful effector mechanisms of the mammalian immune system. Due to a combination of genetic predisposition and environmental stimuli, approximately 20% of the U.S. population is prone to develop an abnormally strong immediate hypersensitivity, a condition known as allergy. Physiological symptoms include increased vascular permeability, vasodilation, smooth muscle contraction, and local inflammation. These and other IgE dependent reactions can cause allergic diseases like allergic rhinitis (hay fever), asthma, atopic dermatitis (chronic skin irritations) and in the most severe cases can lead to anaphylactic shock, causing death of the individual by asphyxiation and cardiovascular collapse. Common environmental allergens are pollen, dust mites, certain foods, animal dander, fungal spores, and insect venoms.

The first exposure to a specific antigen can lead to the sensitization of the individual. The allergen binds with low specificity to pre-existing IgE in the plasma. This complex interacts with the low affinity receptor FcεRII on antigen presenting cells (APC). The antigen is internalized, proteolytically processed and transported to the surface of the APC by class II MHC molecules. Fragments of the antigen are thereby presented to CD4+ T helper cells which in turn activate IgE committed B cells to produce antigen-specific IgE. Normally IgE occurs in the human plasma at a concentration of about 0.2 mg/ml but in atopic patients this level can rise to a concentration of over 10 mg/ml.

Re-exposure to the allergen results in tight binding to the allergen-specific IgE present on the high-affinity receptor FcεRI on the surface of mast cells. Multivalent allergens cause the crosslinking of several receptors in the cell membrane. This triggers an intracellular signaling cascade, leading ultimately to the release of preformed mediators from cytoplasmic granules and the secretion of newly synthesized mediators. These mediators, notably histamines, leukotrienes, prostaglandins, and proteases, in turn cause the wide spectrum of symptoms of the allergic response. Furthermore, the release of chemotactic cytokines from the mast cell attracts and activates inflammatory cells to the location of antigen exposure. Finally, the release of IL-4 activates B cells to produce more antigen-specific IgE, thereby amplifying the allergic response. For a review, see Sutton et al. (1993) Nature 366: 421–428.

Mounting evidence indicates that the IgE system has evolved to cope primarily with infections by parasitic worms like *Schistosoma mansoni*. In the absence of such parasites, IgE mediated responses seem to be dispensable and frequently lead to pathologic consequences. Supporting this hypothesis is the fact that murine strains deficient in IgE or the IgE high-affinity receptor (Dombrowicz, et al. (1993) Cell 75: 969–976) lack the anaphylactic response, but appear otherwise normal.

IgE is a 190 kD antibody consisting of two ε heavy chains (70 kD) and two light chains (25 kD). The heavy chains contain one variable domain ($V_H$) and four constant domains ($C_H1$ to $C_H4$). The light chains contain one variable domain ($V_L$) and one constant domain ($C_L$). Each of these immunoglobulin domains consists of about 100 residues and is stabilized by intramolecular sulfur bridges. The heavy and light chains are connected by intermolecular sulfur bridges.

The IgE molecule can be subdivided into the $F_{AB}$ (antigen binding) region, containing the variable and the first constant domains and the $F_C$ (crystalline) region, consisting of the remaining constant domains. The antigen binds to hypervariable sites within the variable region, whereas the IgE receptors bind to the $F_C$ region. The high-affinity IgE receptor FcεRI contacts a dodecapeptide sequence located at the N-terminus of the $C_H3$ domain and the low affinity IgE receptor FcεRII binds to the middle portion of the same domain (reviewed in Sutton, et al., supra).

The IgE molecule is significantly bent, reducing its predicted length from 17.5 nm for a planar molecule to 7 nm. This bend occludes one of the two potential FcεRI receptor binding sites resulting in a monovalent IgE molecule which, in the absence of a multivalent allergen, cannot crosslink receptor molecules to initiate the allergic response.

To allow the antigen mediated triggering of the allergic response, IgE must form a complex with the high affinity receptor, FcεRI. FcεRI consists of four transmembrane polypeptides: a, b, and $g_2$. The a subunit, FcεRI(a), contains two extracellular immunoglobulin domains and it is the second domain, a(2), that binds to the convex site of the IgE molecule. The dissociation constant of this interaction is approximately $10^{-10}$M (Sutton, et al., supra). The b and g chains of FcεRI are necessary to anchor the receptor in the cell membrane, to allow receptor crosslinking, and for signal transduction to initiate the release of mediators from mast cells.

To inhibit immediate hypersensitivity numerous steps of the pathway can be targeted. It should be possible to prevent the synthesis of IgE by binding to and blocking the action of IL-4 or the IL-4 receptor, to prevent mast cell and basophil stimulation by blocking IgE or the FcεRI IgE receptor, to prevent release of mediators by blocking a step of the intracellular signaling pathway, or to prevent physiological responses of patients by blocking the released mediators. This work demonstrates the use of high-affinity oligonucleotides to human IgE to inhibit the interaction of IgE with the FcεRI receptor.

BRIEF SUMMARY OF THE INVENTION

The present invention includes methods of identifying and producing nucleic acid ligands to Immunoglobulin E (IgE)

and the nucleic acid ligands so identified and produced. More particularly, RNA sequences are provided that are capable of binding specifically to IgE.

Also included in this invention are RNA ligands of IgE that are inhibitors of IgE receptor binding. Specifically, RNA ligands are identified and described which inhibit the interaction of IgE with the FceRI IgE receptor and thereby inhibit the allergic response ellicited by IgE.

Further included in this invention is a method of identifying nucleic acid ligands and nucleic acid ligand sequences to IgE comprising the steps of (a) preparing a candidate mixture of nucleic acids, (b) partitioning between members of said candidate mixture on the basis of affinity to IgE, and (c) amplifying the selected molecules to yield a mixture of nucleic acids enriched for nucleic acid sequences with a relatively higher affinity for binding to IgE.

More specifically, the present invention includes the RNA ligands to IgE identified according to the above-described method, including those ligands listed in Table 1 (SEQ ID NOS: 7–41 and 43–48). Also included are RNA ligands to IgE that are substantially homologous to any of the given ligands and that have substantially the same ability to bind IgE and inhibit IgE receptor binding. Further included in this invention are RNA ligands to IgE that have substantially the same structural form as the ligands presented herein and that have substantially the same ability to bind IgE and inhibit IgE receptor binding.

The present invention also includes modified nucleotide sequences based on the RNA ligands identified herein and mixtures of the same.

DETAILED DESCRIPTION OF THE INVENTION

This application describes high-affinity nucleic acid ligands to IgE identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, U.S. Pat. No. 5,475,096 entitled Nucleic Acid Ligands, U.S. patent application Ser. No. 07/931,473, filed Aug. 17, 1992, entitled Nucleic Acid Ligands, now U.S. Pat. No. 5,270,163, (see also PCT/US91/04078). These applications, each specifically incorporated herein by reference, are collectively called the SELEX patent applications. In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX patent applications describe and elaborate on this process in great detail. Included are targets that can be used in the process; methods for partitioning nucleic acids within a candidate mixture; and methods for amplifying partitioned nucleic acids to generate enriched candidate mixture. The SELEX patent applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of IgE. In the Example section below, the experimental parameters used to isolate and identify the nucleic acid ligands to IgE are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992, now U.S. Pat. No. 5,496,938, ('938) methods are described for obtaining improved nucleic acid ligands after SELEX has been performed. The ('938), entitled Methods of Producing Nucleic Acid Ligands, is specifically incorporated herein by reference.

In the present invention, a SELEX experiment was performed in search of RNA with specific high affinity for IgE from a degenerate library containing 40 or 60 random positions (40N or 60N). This invention includes the specific RNA ligands to IgE shown in Table 1 (SEQ ID NOS: 7–41 and 43–48), identified by the methods described in Examples 1 and 2. The scope of the ligands covered by this invention extends to all nucleic acid ligands of IgE, modified and unmodified, identified according to the SELEX procedure. More specifically, this invention includes nucleic acid sequences that are substantially homologous to the ligands shown in Table 1. By substantially homologous it is meant a degree of primary sequence homology in excess of 70%, most preferably in excess of 80%. A review of the sequence homologies of the ligands of IgE shown in Table 1 shows that sequences with little or no primary homology may have substantially the same ability to bind IgE. For these reasons, this invention also includes nucleic acid ligands that have substantially the same ability to bind IgE as the nucleic acid ligands shown in Table 1. Substantially the same ability to bind IgE means that the affinity is within a few orders of magnitude of the affinity of the ligands described herein. It is well within the skill of those of ordinary skill in the art to determine whether a given sequence—substantially homologous to those specifically described herein—has substantially the same ability to bind IgE.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 9, 1993, now abandoned entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process.

The nucleic acid ligands to the IgE protein described herein are useful as pharmaceuticals and as diagnostic reagents.

The following Examples are provided to explain and illustrate the present invention and are not intended to be limiting of the invention.

Example 1 describes the various experimental procedures used in the subsequent examples. Example 2 describes a representative method for identifying RNA ligands by the SELEX method which bind IgE and determines the affinities the ligands have for IgE. Example 3 maps which regions of the ligands are necessary for IgE binding. Example 4 demonstrates the specificity of the ligands for Human IgE. Example 5 demonstrates that the ligands of the invention are capable of inhibiting the interaction between IgE and the FcεRI receptor.

EXAMPLE 1

Experimental Procedures

The experimental procedures provided in this example will be used in subsequent examples and are provided here to streamline the description.

A. Materials and Methods

Human IgE used in this SELEX procedure was purchased from Athens Research Technology. Biotinylated TAN IgE and the RBL cell lines, untransfected or transfected with the FcεRI receptor were a generous gift from Dr. Kinet (NIH). 2' $NH_2$ modified CTP and UTP were prepared according to the method of Pieken et al. (1991) Science 253: 314–317). DNA oligonucleotides were synthesized by Operon Technologies (Alameda, Calif.). All other reagents and chemicals were purchased from standard commercial sources.

B. SELEX

The SELEX procedure has been described in detail in U.S. Pat. No. 5,270,163. For the IgE experiments, the DNA templates were designed to contain 40 or 60 random nucleotides, flanked by 5' and 3' regions of fixed structure (shown in Table 2) designated 40N7 (SEQ ID NO: 1) and 60N7 (SEQ ID NO: 2), respectively. The fixed regions include DNA primer annealing sites for PCR and cDNA synthesis as well as the consensus T7 promoter region to allow in vitro transcription. Single-stranded DNA molecules were converted into double-stranded transcribable templates by PCR amplification. PCR conditions were 50 mM KCl, 10 mM Tris-Cl, pH 9, 0.1% Triton X-100, 3 mM $MgCl_2$, 0.5 mM of each dATP, dCTP, dGTP, and dTTP, and contained 0.1 units/μl of Taq DNA polymerase. Transcription reactions contained 5 μM DNA template, 5 units/μl T7 RNA polymerase, 40 mM Tris-Cl (pH 8.0), 12 mM $MgCl_2$, 5 mM DTT, 1 mM spermidine, 0.002% Triton X-100, 4% PEG 8000, 2 mM each of 2'-OH ATP, 2'-OH GTP, 2'-$NH_2$ CTP, 2'-$NH_2$ UTP, and 0.25 μM α-$^{32}$P 2'OH ATP. The RNA molecules were incubated with IgE protein in modified phosphate buffered saline (PBS), modified to contain 1 mM $Mg^{2+}$ ions, (138 mM NaCl, 2.7 mM KCl, 8.1 mM $Na_2HPO4$, 1.1 mM $KH_2PO4$, 1 mM $MgCl_2$, pH 7.4) for 10 min to allow binding to occur. IgE-RNA complexes were separated from unbound RNA by nitrocellulose filter partitioning. Bound RNA was isolated from filters by phenol/urea extraction. The RNA was reverse transcribed into cDNA by AMV reverse transcriptase (AMV RT) at 48° C. for 60 min in 50 mM Tris-Cl (pH 8.3), 60 mM NaCl, 6 mM $Mg(OAc)_2$, 10 mM DTT, 50 pmol DNA primer, 0.4 mM each of dNTPs, and 1 unit/μl AMV RT. PCR amplification of this cDNA resulted in approximately 500 pmol double-stranded DNA which was used to initiate the next round of SELEX.

C. Nitrocellulose Filter Partitioning

For isolation of RNA molecules that bind tightly to IgE, the nitrocellulose filter partitioning method was used as described in the SELEX patent applications. Filter discs (nitrocellulose/cellulose acetate mixed matrix, 0.45 μm pore size, Millipore Corporation, Bedford, Mass.) were placed into a vacuum manifold and wetted with 5 ml of modified PBS buffer. $^{32}$P labeled RNA pools were incubated with serial dilutions of IgE in modified PBS for 10 min at 37° C. and aspirated through the filter discs which was followed immediately by a 5 ml modified PBS wash. The filter discs were air-dried and counted in a liquid scintillation counter (Beckmann Instruments, Palo Alto, Calif.).

To obtain equilibrium dissociation constants of RNA ligands to IgE the binding reaction:

| R.P → R + P | R = RNA |
| | P = Protein |
| | $K_D$ = dissociation constant | is converted to an equation for the fraction of RNA bound at equilibrium:

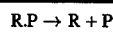

$$q=(f/2R_T)*(P_T+R_T+K_D-((P_T+R_T+K_D)^2-4P_TR_T)^{1/2})$$

q=fraction of RNA bound
$P_T$=total protein concentration
$R_T$=total RNA concentration
f=retention efficiency of RNA-protein complexes The average retention efficiency for RNA-IgE complexes on nitrocellulose filters is 0.8. $K_D$s were determined by least

7 square fitting of the data points using the KALEIDA-GRAPH™ graphic program (Synergy Software, Reading, Pa.).

D. Cloning and Sequencing

During the last round of SELEX, PCR of cDNA was performed with the primers shown in Table 2 which contain recognition sites for the restriction endonucleases HindIII (5' primer 5P7H (SEQ ID NO: 5)) and BamHI (3' primer 3P7B (SEQ ID NO: 6)). Using these restriction sites the DNA sequences were inserted directionally into the pUC19 vector. These recombinant plasmids were transformed into *E. coli* SURE™ strain (Stratagene, La Jolla, Calif.). Plasmid DNA was prepared with the CLEARCUT™ miniprep kit (Stratagene, La Jolla, Calif.) and about 80 clones were sequenced with the SEQUENASE™ sequencing kit (United States Biochemical Corporation, Cleveland, Ohio).

E. Ligand Truncation

Truncation experiments were carried out to determine the minimal sequence necessary for high affinity binding of the RNA ligands to IgE. For 3' boundary determination, RNA ligands were 5' end-labeled with $\gamma$-$^{32}$P-ATP using T4 polynucleotide kinase. 5' boundaries were established with 3' end-labeled ligands using $\alpha$-$^{32}$P-pCp and T4 RNA ligase. After partial alkaline hydrolysis, radiolabeled RNA ligands were incubated with IgE at concentrations ranging from 1 nM to 150 nM and protein-bound RNA was separated by nitrocellulose partitioning. RNA truncates were analyzed on a high-resolution denaturing polyacrylamide gel. A ladder of radioactively labeled ligands terminating with G-residues was generated by partial RNase T1 digestion and was used as markers.

F. IgE Receptor Binding Assay

A cell-based enzyme linked immunosorbent assay (ELISA) was used to measure the ability of the high-affinity RNA ligands to inhibit binding of IgE to the FceRI receptor. Rat basophilic leukemia (RBL) cell-line SX-38 which expresses the $\alpha$, $\beta$ and $\gamma$ subunits of the human FceRI IgE receptor was plated at a concentration of $10^5$ cells per well in 96 well flat-bottom microtiter plates. After overnight growth the cells were washed three times in modified PBS and incubated for one hour at 37° C. in 30 µl of 1.5 mg/µl biotinylated TAN IgE. The cells were washed 3 more times and incubated in 30 µl of 1/100 dilution of horseradish peroxidase conjugated to avidin (Molecular Probes, Eugene, Oreg.) for one hour at 37° C. After three final washes 30 µl of 3,3', 5,5'-tetramethylbenzidine (TMB) substrate (Kirkegaard and Perry Laboratories, Gaithersburg, Md.) were added as a chromogenic substrate and the plate was immediately transferred to the microtiter plate reader (Bio-Tek Instruments, Winooski, Vt.) for analysis. The absorbance at 630 nM was measured every 60 sec over a time span of 15 min. The rate of color development is an indication of the extent of IgE binding to the FceRI receptor and was determined from the linear part of absorbance versus time graphs (data not shown). To test the effectiveness of RNA ligands to inhibit IgE binding to the receptor, the biotinylated TAN IgE was pre-incubated with RNA at concentrations ranging from $10^{-5}$M to $3.3\times10^{-9}$M for 30 min at 37° C. As control reactions addition of RNA or IgE were omitted (maximum rate and background rate, respectively). The inhibition activities of the RNA ligands were determined using the following formula:

$I_B = (R_R - B_R)/(M_R - B_R) *100$  $I_B$ = relative percentage IgE bound $R_R$ = reaction rate
$B_R$ = background rate
$M_R$ = maximum rate Substituting transfected RBL SX-38 cells with the untransfected parental cell-line resulted in reaction rates similar to the background rate (data not shown). Values for the inhibition constant ($K_i$) were calculated based on the following estimates: $10^5$ cells per well and $10^5$ receptors per cell in 30 µl volume, resulting in a receptor concentration of $5\times10^{-10}$M. The IgE concentration in this assay was $8\times10^{-12}$M and the dissociation constant for the IgE/receptor complex is $10^{-10}$M $10^{-10}$M.

EXAMPLE 2

RNA Ligands to IGE

A. SELEX In order to generate stable ligands to human IgE two SELEX experiments were performed with 2'-NH$_2$ pyrimidine modified RNA molecules using the methods described in Example 1. As shown in Table 2, these RNA pools differ in the number of random bases present in the central portion of the molecules: 40 nucleotides in the 40N7 (SEQ ID NO: 1) SELEX and 60 nucleotides in the 60N7 (SEQ ID NO: 2) SELEX experiment. The starting pools of $3\times10^{14}$ RNA molecules (500 pmol) bind IgE with approximate affinities of greater than 50 mM. After 9 rounds of SELEX, the affinities of the evolving pools had improved about two orders of magnitude and did not shift further in subsequent rounds. Round 9 RNA was bulk sequenced and found to be non-random. Therefore, cDNA from this round was PCR amplified with primers containing restriction sites and cloned into pUC19. About 35 clones from each SELEX experiment were sequenced as shown in Table 1. The sequences were inspected by eye and analyzed using computer programs which perform alignments.

B. RNA Sequences 25 out of 35 (40N7 SELEX) and 30 out of 34 (60N7 SELEX) sequenced clones were found to be unique. As shown in Table 1, these unique clones can be divided into four classes: high-affinity IgE ligand Groups A (SEQ ID NOS: 7–18) and B (SEQ ID NOS: 19–28), a group of unrelated high-affinity IgE ligands called orphan sequences (SEQ ID NOS: 29–41) and nitrocellulose binding ligand Group C (not shown). It is interesting to note that all groups contain members of both 40N7 (SEQ ID NO: 1) and 60N7 (SEQ ID NO: 2) sequences. This indicates that independent SELEX experiments can result in the isolation of essentially identical ligands.

To crudely screen the ligands for their ability to bind to IgE, 2-point $K_D$s were determined for all clones (data not shown). Group C ligands containing the consensus motif: 5' G-G-G-($N_{3-5}$)-G-U/C-G-G-A/U-G-G-G-G 3' (SEQ ID NO: 42) were found to have high affinities for nitrocellulose instead of IgE and were not further analyzed.

Group A and group B ligands show characteristic conserved consensus domains of 10 and 20 nucleotides, respectively, immediately adjacent to the 5' fixed region as shown in Table 1. The conserved domains are:

5' GUG UGA AUG GUG UUG UGA GG 3' (SEQ ID NO: 43)

5' GUG UGG GGC G 3' (SEQ ID NO: 44)

The remaining bases of the variable regions 3' to these conserved stretches show no observable sequence conservation and are, therefore, unlikely to contribute to the specific binding of IgE.

C. Affinities

The RNA ligands of group A, group B and most orphan sequences are high affinity IgE ligands and show very little binding to nitrocellulose. Dissociation constants for representative members of Group A and Group B as well as orphan sequences were determined by nitrocellulose filter binding experiments and the dissociation constants are listed in Table 3. Group A ligands show an average $K_D$ of approximately 150 nM, Group B ligands had an average $K_D$ of approximately 35 nM and orphan ligands had $K_D$s ranging from 50 nM to 250 nM.

EXAMPLE 3

Ligand Truncation

To determine the minimal sequence information necessary for high-affinity binding to IgE, truncation analysis was performed as described in Example 1 on representative members of Group A (IGEL1.1 (SEQ ID NO: 7) and IGEL31.1 (SEQ ID NO: 18)) and Group B (IGEL2.1 (SEQ ID NO: 20) and IGEL48.1 (SEQ ID NO: 27)). Table 1 shows that the 3' boundaries of the truncated ligands (SEQ ID NOS: 45 and 46) are located, as expected, precisely at the end of the conserved consensus sequence motifs (SEQ ID NO: 43) and (SEQ ID NO: 44), in the variable region. This concurs with the hypothesis that these conserved sequence motifs are necessary for tight binding to IgE, whereas the degenerate remainder of the variable regions and the 3' fixed regions are dispensable. The 5' boundary determinations revealed that the entire 5' fixed regions, with the possible exception of the first three guanidine residues, are involved in binding to IgE. For technical purposes, further experiments were conducted with truncated ligands consisting of the intact 5' fixed region and the consensus domain, called IGEL1.2 (SEQ ID NO: 47) (Group A truncate of IGEL1.1) and IGEL2.2 (SEQ ID NO: 48) (Group B truncate of IGEL2.1). Since these truncates are not missing any 5' sequence information critical for transcription initiation, they transcribe efficiently and yield several hundred RNA molecules per DNA template in overnight in vitro transcription reactions (data not shown). Representative binding data for these truncated RNA ligands in direct comparison with their full-length counterparts are shown in Table 3. While the $K_D$ of IGEL2.2 is essentially unaffected by the truncation, IGEL1.2 actually binds several fold better as a truncate compared to the full-length IGEL1.1 ligand. This result demonstrates that the removal of nucleotides which are not contributing to the binding of a protein can increase the affinity of this interaction, possibly by allowing a tighter fit of the RNA to the surface of the protein.

EXAMPLE 4

Specificity of RNA Ligands to Human IGE

To test the specificity of the high-affinity interaction between the RNA ligands and human IgE, binding experiments were performed with different immunoglobulins as described in Example 1. Table 4 summarizes the results of these studies with rat, murine and a human-murine hybrid IgE. The $K_D$s for murine and rat IgE are estimated to be greater than 5 µM which is at least two orders of magnitude higher than the corresponding dissociation constants to human IgE. Furthermore, IgE ligands do not bind significantly to human IgG, a different immunoglobulin isotype (data not shown). These results indicate that the RNA ligands are very specific for human IgE and do not interact efficiently with related molecules.

In order to localize which part of the IgE molecule the RNA ligands are contacting, binding experiments were carried out with a hybrid IgE molecule. The light chains and the variable region of this TAN IgE are murine derived, whereas the constant portion of the heavy chains are human. As shown in Table 4, the affinities of ligands IGEL1.1 (SEQ ID NO: 7) and IGEL1.2 (SEQ ID NO: 47) are equivalent to those determined for the entirely human IgE. These results indicate that ligands IGEL1.1 and IGEL1.2 are contacting IgE at the $F_c$ portion. This part of the IgE molecule also harbors the contact region with the FcεRI receptor, making it potentially possible to competitively inhibit IgE binding to the receptor.

EXAMPLE 5

Inhibition of the IGE-FCεRI Interaction

To directly test the ability of the RNA ligands to competitively inhibit the binding of IgE to the FcεRI receptor, a tissue culture cell based assay was performed as described in Example 1. Briefly, rat basophilic leukemia (RBL) cells that are expressing the human FcεRI receptor on the cell surface were incubated with biotinylated IgE. Using streptavidin conjugated horseradish peroxidase, the relative amount of IgE bound to the receptor can be determined by measuring the rate of conversion of a chromogenic substrate. The rate in the absence of inhibiting RNA is defined as 100% activity and the rate in the absence of IgE is used to calculate the background which is subtracted from the conversion rates. The RNA species to be tested for competitive inhibition were pre-incubated with the IgE before the mixture was added to the RBL cells. Random RNA, the 40N7 (SEQ ID NO: 1) and 60N7 (SEQ ID NO: 2) starting pools, do not show any significant inhibition of IgE binding to the FcεRI receptor (data not shown). However, Group A ligands IGEL1.1 (SEQ ID NO: 7) and IGEL1.2 (SEQ ID NO: 47) do inhibit this interaction as shown in Table 4. The inhibitory dissociation constants ($K_i$) determined in this assay, 44 nM for IGEL1.1 and 21 nM for IGEL1.2, correspond well with the previously calculated $K_D$ values of 77 nM and 36 nM, respectively, of these ligands for TAN IgE. These results show that binding of Group A ligands to IgE causes competitive inhibition of the interaction with the FcεRI receptor. The orphan ligands tested in this assay show varying degrees of inhibition and most of them appear to be weaker inhibitors than IGEL1.1 and IGEL1.2. Group B ligands IGEL2.1 (SEQ ID NO: 20) and IGEL2.2 (SEQ ID NO: 48) do not show significant inhibition (data not shown) although they bind IgE tightly. This observation indicates that Group A and Group B ligands either bind IgE at different areas or that the binding orients the Group B ligands differently as to not allow inhibition of the IgE/receptor interaction.

TABLE 1

IgE Binding Ligands

| * | ** | | SEQUENCE*** |
|---|---|---|---|
| | | | Group A Sequences |
| 7 | 1.1 | | GGGAGGACGAUGCGGGGUGUGAAUGGUGUGUGUGAGGUUACUGUGGUGCGCUGCAGACGACUCGCCCGA |
| 8 | 21.1 | | GGGAGGACGAUGCGGGGUGUGAAUGCGGUGUGUGUGAGGUUACUGUACUUCGUGGCUGCAGACGACUCGCCCGA |
| 9 | 22.1 | | GGGAGGACGAUGCGGGGUGUGAAUGCGGUGUGUGUGAGGAGCCUAAAUACGGAUUGGUCAGACGACUCGCCCGA |
| 10 | 23.1 | | GGGAGGACGAUGCGGGGUGUGAAUGGUGUGAUGAGGUCCCAGGCGAAGUUCCCAGGCCAGACGACUCGCCCGA |
| 11 | 24.1 | | GGGAGGACGAUGCGGGGUGUGAAUGGUGUGCGAGGCAUGCAGGGCUGUGGUCAGACGACUCGCCCGA |
| 12 | 25.1 | | GGGAGGACGAUGCGGGGUGUGAAUGCGGUGUGGAGGACUUAUCAGGCUGUGCGUGACGACUCGCCCGA |
| 13 | 26.1 | | GGGAGGACGAUGCGGGGUGUGAAUGGUGUGAGGUUACGCACUUCGCGCAGACGACUCGCCCGA |
| 14 | 27.1 | | GGGAGGACGAUGCGGGGUGUGCAUGGUGUGAGGCUGAGUAUAGGGGCCUGCGUCAGACGACUCGCCCGA |
| 15 | 28.1 | | GGGAGGACGAUGCGGGGUGUGAAUGCGGUGUCGUGAGGAGGAUUCGACAUGAGCGAUCAGACGACUCGCCCGA |
| 16 | 29.1 | | GGGAGGACGAUGCGGGGUGUCGAUGGUGUGAGGCAAAAUAACCAGCGCCAUAUUCGCGCCAUGUUGGCCGUGCAUACAGACGACUCGCCCGA |
| 17 | 30.1 | | GGGAGGACGAUGCGGGGUGUGAAUGCGGUGUGGAGGAGUGAAAUAUAGGGAUACCCUUAACAACUGCUGGGGUCAGACGACUCGCCCGA |
| 18 | 31.1 | | GGGAGGACGAUGCGGGGUGUGAAUGCGGUGUGAAUGGUGUGAGGUUCUCGACUGUGUGUCUAGCCGUACUUUAGCCUCCGGCCAGACGACUCGCCCGA |
| 43 | Consensus | | GUGUGAAUGGUGUUGUGAGG |
| 45 | Truncated | | AGGACGAUGCGGGUGUGAAUCGUGUGUGAGG |
| 47 | 1.2 | | GGGAGGACGAUGCGGGGUGUGAAUGGUGUUGUGAGG |
| | | | Group B Sequences |
| 19 | 41.1 | | GGGAGGACGAUGCGGGUGAGGGCGAAUGGAGAACAUGAGAACAAGAGAAAUGCGGACUGCAGACGACUCGCCCGA |
| 20 | 2.1 | | GGGAGGACGAUGCGGGUGGGGCGAAUGGAAAAAUGCGACUGACGACGACUCGCCCGA |
| 21 | 42.1 | | GGGAGGACGAUGCGGGAGUGCGGGGCGAAUGGAAAUGUUGAGACGAUGAAAGACUGACGACUCGCCCGA |
| 22 | 43.1 | | GGGAGGACGAUGCGGGUGCGGGCGAUUCAUAUCAACUGCUAAGGUCACGGGUCAGACGACUCGCCCGA |
| 23 | 44.1 | | GGGAGGACGAUGCGGGUGCGGGCGAGUAUUGCCGAUAUAAUGAACUUGGCUCUGGAUUUGCCACUUGAUUUGGACAUCAGAGUCGAAGUGAGACCGACGACUCGCCCGA |
| 24 | 45.1 | | GGGAGGACGAUGCGGGGAGUGGGGCGGCUUGGACCUUGGAAUAACUAUGGUCGUUAAAUUGUCCCUGUCCGGUGUCACCAACCUUGUCAGACGACUCGCCCGA |
| 25 | 46.1 | | GGGAGGACGAUGCGGGGAGUGGGGGCGUAAAUGUCGUUAAAUUGUCGUUAACCAGCGACUGCCUGUAACAAAUCGAGACGACUCGCCCGA |
| 26 | 47.1 | | GGGAGGACGAUGCGGGGUGUGGGGCGGCGAUAAUGAGAGAAAUCAGAGUGAACUAGAGUGAAAUCCAGUGAGCCAGAACUGAGGUGUUGCCAGACGACUCGCCCGA |
| 27 | 48.1 | | GGGAGGACGAUGCGGGGUGCGGAGUGGGGGCGAUGAGAGUGAGUGAAAUCCAGUAGCCAGAACUGUGAGCUGUGCCAGACGACUCGCCCGA |
| 28 | 49.1 | | GGGAGGACGAUGCGGGGUGCGGGGCGGAAUGAGAGUAGAGAGGUGAAAUCCAGUCUGCAGAGCGACUCGCCCGA |
| 44 | Consensus | | GUGUGGGGCG |
| 46 | Truncated | | AGGACGAUGCGGGUGUGGGGCG |
| 48 | 2.2 | | GGGAGGACGAUGCGGGUGUGGGGCG |
| | | | Orphan Sequences |
| 29 | 3.1 | | GGGAGGACGAUGCGGUCCAUCGGAUUAGGCGGUCGUGCUGGUGUGUAGUGGCAGAGGACUCGCCCGA |
| 30 | 4.1 | | GGGAGGACGAUGCGGACGUAGCGUAGGCGUAGCCUGCAGCCGUAGGCGGACCGAGAAUCCGAGAAUCAGAGGACGACUCGCCCGA |
| 31 | 5.1 | | GGGAGGACGAUGCGGGAUCGGUAUCGGUAGUCGUGAAGGGUCCGACGGUGCAGAGGACGACUCGCCCGA |
| 32 | 6.1 | | GGGAGGACGAUGCGGGACGAUGCGGACGAUCGGAUCGGACGUUGAGGGCCUGUGACGGUAGUCGGAAUCCGAGAUCAGAGGACGACUCGCCCGA |
| 33 | 7.1 | | GGGAGGACGAUGCGGACGAUGCGGACGAUCGGAUCUGCCCGUGAACACAGUAGGUAAGGAUGCGCGAACACGGACGACUCGCCCGA |
| 34 | 8.1 | | GGGAGGACGAUGCGGACCCCGGGGACCGUCGAGCGUACGGCCUAGACGCGUAGGCGACGCACAGCGAACACGGACGACUCGCCCGA |
| 35 | 9.1 | | GGGAGGACGAUGCGGCGGCCACGCGGGUUAGGGAUCGGGACAGCAGCACAAAUGAAUUGAUUGAUAUCGCACCUGGACGACUCGCCCGA |
| 36 | 10.1 | | GGGAGGACGAUGCGGGGCCACGCGGUAUCGGGUUAGGCAGAUCCGGACAGCAGCACAAAUCGAAUUGAUUCGCACCUGGACGGUCAGAGACGACUCGCCCGA |

TABLE 1-continued

IgE Binding Ligands

| * | ** | SEQUENCE*** |
|---|---|---|
| 37 | 11.1 | GGGAGGACGAUGCGGAAACAGCACGAGUGUACCUAAGACAGGCGAUGGCACUCGUGGUCGAAAUCAUAUAGUGAUGCAGACGACUCGCCCGA |
| 38 | 13.1 | GGGAGGACGAUGCGGACGGGCGGGCGAAUCAUGCAGGAGAGCGUGUACAUCCAUUCCAUCGUGGUCAGACGACUCGCCCGA |
| 39 | 15.1 | GGGAGGACGAUGCCGAGGCGACAGGGUAGGGAAGAUCGUCUGAAGUAUGCGUCCUUCCAGCCCGUCAGACGACUCGCCCGA |
| 40 | 16.1 | GGGAGGACGAUGCCGUGGAGCCUUUAGGGGAGCCUUUAGGGGGAUCGCACCUGAAUUGCAGCUCAUGUAAUCUCGACUGUGUGACGACUCGCCCGA |
| 41 | 17.1 | GGGAGGACGAUGCGGUGGAGCCUUUAGGGGGAUCGCACCUGAUAGACGCAGUAUCGAUAGACACAAAGACCGAUAGACGACGUGCCCAGACGACUCGCCCGA |

*SEQ ID NO
**IGEL numbers
***nucleotide abbreviations C and U actually depict the modified nucleotides 2'-NH$_2$—C and 2'-NH$_2$—U

TABLE 2

| SEQ ID NO: | Nucleic Acid Sequence |
|---|---|
| | Starting RNAs: |
| | 40N7: |
| 1 | 5' GGGAGGACGAUGCGG [-40N-] CAGACGACUCGCCCGA 3' |
| | 60N7: |
| 2 | 5' GGGAGGACGAUGCGG [-60N-] CAGACGACUCGCCCGA 3' |
| | SELEX PCR Primers: |
| | 5P7: |
| 3 | 5' TAATACGACTCACTATAGGGAGGACGATGCGG 3' |
| | 3P7: |
| 4 | 5' TCGGGCGAGTCGTCTG 3' |
| | Cloning PCR Primers: |
| | 5P7H: |
| 5 | 5' CCGAAGCTTAATACGACTCACTATAGGGAGGACGATGCGG 3' |
| | 3P7B: |
| 6 | 5' GCCGGATCCTCGGGCGAGTCGTCTG 3' |

TABLE 3

| Group | SEQ ID NO: | Ligand | Dissociation Constant |
|---|---|---|---|
| A | 7 | IGEL1.1 | 138 nM |
| | 12 | IGEL25.1 | 186 nM |
| | 16 | IGEL29.1 | 141 nM |
| | 18 | IGEL31.1 | 134 nM |
| B | 20 | IGEL2.1 | 41 nM |
| | 23 | IGEL44.1 | 34 nM |
| | 27 | IGEL48.1 | 30 nM |
| | 28 | IGEL49.1 | 39 nM |
| Orphans | 29 | IGEL3.1 | 56 nM |
| | 30 | IGEL4.1 | 87 nM |
| | 31 | IGEL5.1 | 145 nM |
| | 33 | IGEL7.1 | 142 nM |
| | 34 | IGEL8.1 | 225 nM |
| | 35 | IGEL9.1 | 105 nM |
| | 36 | IGEL10.1 | 69 nM |
| | 37 | IGEL11.1 | 129 nM |
| | 38 | IGEL13.1 | 50 nM |
| Group A Truncate | 47 | IGEL1.2 | 19 nM |
| Group B Truncate | 48 | IGEL2.2 | 44 nM |

TABLE 4

| Protein | Ligand (SEQ ID NO:) | Dissociation Constant | Inhibition Constant |
|---|---|---|---|
| Murine IgE | IGEL1.2 (47) | ≧5 mM | |
| | IGEL2.2 (48) | ≧5 mM | |
| Rat IgE | IGEL1.2 (47) | ≧5 mM | |
| | IGEL2.2 (48) | ≧5 mM | |
| TAN IgE | IGEL1.1 (47) | 77 nM | 44 nM |
| | IGEL1.2 (48) | 36 nM | 21 nM |

We claim:

1. A method for identifying nucleic acid ligands to Immunoglobulin E (IgE), comprising:

a) preparing a candidate mixture of nucleic acids;

b) contacting said candidate mixture of nucleic acids with IgE, wherein nucleic acids having an increased affinity to the IgE relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acid sequences with relatively higher affinity and specificity for binding to IgE, whereby nucleic acid ligands of IgE may be identified.

2. The method of claim 1 further comprising:

e) repeating steps b), c) and d).

3. The method of claim 1 wherein said candidate mixture is comprised of single-stranded nucleic acids.

4. The method of claim 3 wherein said single-stranded nucleic acids are ribonucleic acids.

5. The method of claim 3 wherein said single-stranded nucleic acids are deoxyribonucleic acids.

* * * * *